United States Patent [19]

Welebir

[11] 4,167,641
[45] Sep. 11, 1979

[54] PREPARATION OF LONG-CHAIN CARBOXYLIC ACIDS AND ALCOHOLS

[76] Inventor: Andrew J. Welebir, 1008 Steeples Ct., Falls Church, Va. 22046

[21] Appl. No.: 939,056

[22] Filed: Sep. 1, 1978

[51] Int. Cl.² .................. C07C 29/00; C11C 1/00
[52] U.S. Cl. .................... 568/884; 260/413; 260/593 R; 568/885
[58] Field of Search ............. 260/593 R, 413 Q, 413; 568/884, 885

[56] References Cited

U.S. PATENT DOCUMENTS

| | | | |
|---|---|---|---|
| 2,080,419 | 5/1937 | Green | 568/885 |
| 2,121,580 | 6/1938 | Berliner et al. | 568/885 |
| 2,395,800 | 3/1946 | Boese et al. | 260/593 R |
| 2,438,894 | 4/1948 | Boese | 562/577 |
| 3,030,416 | 4/1962 | von M. Kusch-Buckberg | 260/593 R |
| 4,104,478 | 8/1978 | Trivedi | 568/885 |

*Primary Examiner*—Joseph E. Evans
*Attorney, Agent, or Firm*—Birch, Stewart, Kolasch and Birch

[57] ABSTRACT

The process for the preparation of long-chain carboxylic acids which can be readily converted to alcohols. Shorter chain acids are converted to the acid chloride which may be further purified. The acid chloride is mixed with an enamine and a hindered tertiary amine in an organic solvent and then acidified to form the beta-diketone after washing the organic phase and removal of the solvent. The beta-diketone is reacted with an inorganic hydroxide or alkali metal alkoxide and acidified to produce the keto acid which can be readily converted to the respective aliphatic acid and alcohol.

10 Claims, No Drawings

PREPARATION OF LONG-CHAIN CARBOXYLIC ACIDS AND ALCOHOLS

BACKGROUND OF THE INVENTION

The present invention relates to the preparation of long-chain carboxylic acids and alcohols. The acids are not only useful in themselves but can also be used to produce the alcohol which can be used to increase crop yields.

To the present date, syntheses of long-chain carboxylic acids containing up to about thirty carbon atoms in a straight chain have not proven to be useful economically when applied to large scale production. All processes involve a keto-acid intermediate. Some older processes show very low yields and involve additions of various half esters, half acid chlorides (or halides) to organometallic intermediates or beta-keto esters. While some other methods show good yields, they produce contaminated products.

It is an object of this invention to produce long-chain carboxylic acids and their alcohols in improved yields and purity.

SUMMARY OF INVENTION

The process of the invention is designed for the preparation of long-chain carboxylic acids which can be readily converted to alcohols. Shorter chain acids are converted to the acid chloride which may be further purified. The acid chloride is mixed with an enamine and a hindered tertiary amine in an organic solvent and then acidified to form the beta-diketone after washing the organic phase and removal of the solvent. The beta-diketone is reacted with an inorganic hydroxide or alkali metal alkoxide and acidified to produce the keto acid which can be readily converted to the respective aliphatic acid and alcohol.

EXAMPLE 1

Lignoceric acid was reacted with 3 equivalents of thionyl chloride for 3 hr. at 50–60 degrees in 300 ml per mole of anhydrous chloroform. Excess solvent and thionyl chloride is evaporated leaving an amber liquid, used without further purification. One mole of the acid chloride is then dissolved in 500 ml anhydrous, alcohol-free chloroform and added over 2 hr. to a solution of one mole of 1-morpholino-1-cyclohexene and one equivalent of triethyl amine (a tertiary amine) in an equal volume (500 ml) of chloroform. The temperature was maintained between 30 and 40 degrees, and the resulting complex was stirred and refluxed with 500 ml of 3N hydrochloric acid over a 5 hr. period. The organic phase was then separated and washed with water. The resultant organic phase was evaporated on a rotary evaporator leaving the beta-diketone as a brown oil.

The entire quantity of beta-diketone was then added to a solution of 3 mols of sodium hydroxide in 1.5 liters of ethanol over ½ to 1 hours while maintaining the temperature at less than 78° C. The solution is refluxed for 1 to 2 hours and then cooled to 5° C. The resulting precipitate is filtered and washed with methanol and then dried. The free acid is prepared by suspending the salt in hot water and acidifying to pH 2-3 with hydrochloric acid. After filtering and washing with hot water, the product is 7-keto-1-triacontanoic acid which can be further purified by recrystallization with methyl ethyl ketone. The yield is about 82%.

EXAMPLE 2

Lignoceric acid was reacted with 3 equivalents of thionyl chloride for 3 hr. at 50°–60° C. in 300 ml per mole of anhydrous chloroform. Excess solvent and thionyl chloride is evaporated leaving an amber liquid, used without further purification. One mole of the acid chloride is then dissolved in 500 ml anhydrous, alcohol-free chloroform and added over 2 hr. to a solution of one mole of 1-morpholino-1-cyclohexene and one equivalent of tributyl amine (a tertiary amine) in an equal volume (500 ml) of chloroform. The temperature was maintained between 30° and 40°, and the resulting complex was stirred and refluxed with 500 ml of 3N hydrochloric acid over a 5 hr. period. The organic phase was then separated and washed with water. The resultant organic phase was evaporated on a rotary evaporator leaving the beta-diketone as a brown oil.

The entire quantity of beta-diketone was then added to a solution of 3 mols of sodium ethoxide in 1.5 liters of methanol over ½ to 1 hours while maintaining the temperature at less than 78° C. The solution is refluxed for 1 to 2 hours and then cooled to 5° C. The resulting precipitate is filtered and washed with methanol and then dried. The free acid is prepared by suspending the salt in hot water and acidifying to pH 2-3 with hydrochloric acid. After filtering and washing with hot water, the product is 7-keto-1-triacontanoic acid which can be further purified by recrystallization with methyl ethyl ketone. The yield is about 85%.

EXAMPLE 3

Lignoceric acid was reacted with 2 equivalents of phosphorus pentachloride for 1 hr. at 40°–50° in 300 ml per mole of anhydrous chloroform. Excess solvent was removed by distillation while the acid chloride was then collected after further distillation in vacuo as an amber liquid after cooling. One mole of the acid chloride is then dissolved in 500 ml anhydrous, alcohol-free chloroform and added over 2 hr. to a solution of one mole of 1-morpholino-1-cyclohexene and one equivalent of triethyl amine (a tertiary amine) in an equal volume (500 ml) of chloroform. The temperature was maintained between 30 and 40 degrees, and the resulting complex was stirred and refluxed with 500 ml of 3N hydrochloric acid over a 5 hr. period. The organic phase was then separated and washed with water. The resultant organic phase was evaporated on a rotary evaporator leaving the beta-diketone as a brown oil.

The entire quantity of beta-diketone was then added to a solution of 3 mols of potassium hydroxide in 1.5 liters of ethanol over ½ to 1 hours while maintaining the temperature at less than 78° C. The solution is refluxed for 1 to 2 hours and then cooled to 5° C. The resulting precipitate is filtered and washed with methanol and then dried. The free acid is prepared by suspending the salt in hot water and acidifying to pH2-3 with hydrochloric acid. After filtering and washing with hot water, the product is 7-keto-1-triacontanoic acid which can be further purified by recrystallization with methyl ethyl ketone. The yield is at least 80%.

EXAMPLE 4

The sodium salt of the 7-keto-1-triacontanoic acid (such as produced in Examples 1–3 above) in the amount of 0.9 mol is dissolved in 1 liter of diethylene glycol at 150° C. The temperature is reduced to 130° C.; then 150 ml of hydrazine hydrate was added with the reaction mixture being refluxed for 3 to 4 hours to form the hydrazone. Either at this point or during the previous refluxing, about 200 grams of potassium hydroxide is added to the mixture. After the refluxing, the temperature is raised to 195° C. and refluxing is continued for 4 to 12 hours to decompose the hydrazone to the acid chloride. The temperature is then reduced to 100° C. and 2 liters of hot water is added whereafter the acid salt is acidified to about pH 2-3 with 6N hydrochloric acid (to form triacontanoic acid) and filtered. The triacontanoic acid can be further purified by recrystallization from methyl ethyl ketone with a yield of 89% at a purity of about 99% after washing with diethyl ether and a second recrystallization.

EXAMPLE 5

Triacontanol is prepared from triacontanoic acid by suspending 0.1 mol of the acid in 40 ml of anhydrous chloroform followed by the addition of thionyl chloride while maintaining the temperature at 40° C. for 2 hours. Chloroform and excess thionyl chloride were removed in a rotary evaporator, and the resulting acid chloride was reacted with 10 ml of absolute ethanol to form the ester. Excess ethanol was removed in a similar manner, and the ester was dissolved in 100 ml of anhydrous ether.

Powdered lithium aluminum hydride (0.5 mol) was refluxed in 200 ml of anhydrous diethyl ether until most of the solid had dissolved. The solution of the ester was added slowly over 45 min. with vigorous stirring, and the reaction mixture was allowed to reflux overnight. Ethyl acetate (20 ml) was added to react with the unreacted lithium aluminum hydride, and the mixture was decomposed cautiously with 50 ml of 6N HCl with vigorous stirring. To solubilize the resulting alcohol, 50 ml of benzene was added, and the mixture was washed with warm water. The organic layer was filtered through anhydrous sodium sulfate, and an equal volume of acetone was added. Cooling to 5°, followed by filtration produced 1-triacontanol at a yield of about 86%.

EXAMPLE 6

Docosanoic acid was reacted with 3 equivalents of thionyl chloride for 3 hr. at 50-60 degrees in 300 ml per mole of anhydrous chloroform. Excess solvent and thionyl chloride is evaporated leaving an amber liquid, used without further purification. One mole of the acid chloride is then dissolved in 500 ml anhydrous, alcohol-free chloroform and added over 2 hr. to a solution of one mole of 1-morpholino-1-cyclohexene and one equivalent of diethyl cyclohexyl amine in an equal volume (500 ml) of chloroform. The temperature was maintained between 30 and 40 degrees, and the resulting complex was stirred and refluxed with 500 ml of 3N hydrochloric acid over a 5 hr. period. The organic phase was then separated and washed with water. The resultant organic phase was evaporated on a rotary evaporator leaving the beta-diketone as a brown oil.

The entire quantity of beta-diketone was then added to a solution of 3 mols of sodium hydroxide in 1.5 liters of ethanol over ½ to 1 hours while maintaining the temperature at less than 78° C. The solution is refluxed for 1 to 2 hours and then cooled to 5° C. The resulting precipitate is filtered and washed with methanol and then dried. The free acid is prepared by suspending the salt in hot water and acidifying to pH 2-3 with hydrochloric acid. After filtering and washing with hot water, the product is 7-keto-1-octaconsanoic acid which can be further purified by recrystallization with methyl ethyl ketone. The yield is at least 80%.

The 7-keto-1-octacosanoic acid can be converted to 1-octacosanoic acid in the same manner as the 7-keto-1-triacontanoic acid is converted to 1-triacontanoic acid in Example 4 above and then to the corresponding alcohol as in Examples 5 above and 7 below.

EXAMPLE 7

The acid chloride of 1-triacontanoic acid is converted to the ester by adding methanol or ethanol and stirring for ½ to 1 hour. The alcohol was evaporated on a rotary evaporator leaving ethyl-1-triacontanoate. The ester is then reacted in a pressure vessel under about 250 atmospheres of hydrogen in the presence of a powdered copper chromite catalyst for about 12 hours at 250° C. to produce 1-triacontanol. One part of catalyst is present for every 5 to 10 parts of ester.

It is apparent from the examples herein that the invention includes a number of processes and steps for the formation and treatment of long-chain carboxylic acids. While the preferred starting short-chain acid is lignoceric acid which is used to make 7-keto-1-triacontanoic and 1-triacontanoic acids as well as 1-triacontanol, other short-chain acids can be used to prepare different long-chain carboxylic acids and alcohols containing from 28 to 36 carbons such as octacosanoic acid and octacosanol and hexatricontanoic acid and hexatricontanol.

In the preparation of long-chain carboxylic acids in accordance with the invention, shorter-chain starting acids are first treated with thionyl chloride, phosphorous trichloride or phosphorous pentachloride for two to five hours at temperatures from 30° to 60° C. in the presence of solvents such as anhydrous chloroform or carbon tetrachloride. This produces the acid chloride which can be separated from the excess solvent and chlorinating agent with a rotary exaporator or similar means. In a preferred embodiment, the reacting temperature is from 50° to 60° C. Increasing the concentrations of initial reactants will increase the yield.

The acid chloride is then dissolved in an organic solvent such as chloroform which is added to a solution of an enamine and a hindered tertiary amine also in an organic solvent such as chloroform. The enamine can be 1-morpholino-1-cyclopentene, 1-morpholino-1-cyclohexene or 1-morpholino-1-cycloheptene although the six carbon enamine is preferred. The more hindered the tertiary amine, the greater is the yield. Pyridine and other less hindered amines fail to work. The reaction is maintained at 30° to 40° C. with an ice bath or similar means. Higher concentrations of reactants allow higher temperatures of up to about 60° C. and increase yield. While maintaining the temperature, the resulting complex is stirred and refluxed with hydrochloric acid for 3 to 5 hours, although more rapid stirring will reduce the reaction time. The organic phase is then separated and washed with water with the subsequent recovery of the product beta-diketone.

The beta-diketone is then added to a solution of sodium, potassium or lithium hydroxide in alcohol while keeping the temperature below the boiling point. The yield of this reaction can be increased by substituting an alkoxide for the hydroxide. Sodium hydroxide is the preferred hydroxide among the alkali metal hydroxides which can be used in this reaction. The longer chain alkoxide gives greater yields so that sodium propoxide is better than sodium ethoxide. Sodium is again preferred over the lithium or potassium alkoxides. Almost any alcohol of 6 carbons or less is acceptable including ethylene glycol.

After refluxing, the solution is cooled to 5° C. to precipitate out the salt of the keto acid which is readily isolated by filtering and washing. The free acid can be prepared by merely suspending the salt in hot water and adding hydrochloric acid. If further purification is desired, the acid can be dissolved in heated methyl ethyl ketone and then cooled to recrystallize the purified acid.

The keto acid can be readily converted to the respective carboxylic acid and alcohol by a number of different processes. For example, the Huang-Minlon reduction can be used to form the carboxylic acid.

While preferred embodiments of the invention have been described herein, the invention is not to be construed as limited thereby except as the same may be included in the following claims.

What I claim and desire to protect by Letters Patent is:

1. In a process for the preparation of long-chain carbon compounds, the improvement which comprise:
   a. reacting a 21 to 29 carbon carboxylic acid with a chlorinating agent to form the acid chloride;
   b. separating the acid chloride and reacting it with an enamine and a hindered tertiary amine in an organic solvent while maintaining the reaction temperature at 30° to 60° C.;
   c. removing the solvent and recovering the beta-diketone product;
   d. reacting the beta-diketone with a solution of an alkali metal hydroxide or alkoxide and alcohol; and
   e. recovering the precipitated product.

2. The process of claim 1 wherein the 21 to 29 carbon acid is lignoceric acid.

3. The process of claim 1 wherein the enamine is 1-morpholino-1-cyclohexene.

4. The process of claim 2 wherein the enamine is 1-morpholino-1-cyclohexene.

5. The process of claim 1 wherein the precipitated product is acidified to form the keto acid.

6. The process of claim 5 wherein the 21 to 29 carbon acid is lignoceric acid, the enamine is 1-morpholino-1-cyclohexene, and the keto acid is 7-keto-1-triacontanoic acid.

7. The process of claim 5 wherein the keto acid is reduced to form a long-chain carboxylic acid.

8. The process of claim 7 wherein the long chain carboxylic acid is further reduced to form the respective alcohol.

9. The process of claim 6 wherein the 7-keto-1-triacontanoic acid is reduced to form triacontanoic acid.

10. The process of claim 9 wherein the triacontanoic acid is further reduced to form triacontanol.

* * * * *